United States Patent
Yu et al.

(10) Patent No.: US 6,376,191 B1
(45) Date of Patent: Apr. 23, 2002

(54) MICROARRAY-BASED ANALYSIS OF POLYNUCLEOTIDE SEQUENCE VARIATIONS

(75) Inventors: Zailin Yu, San Leandro; Zaoyuan Peng, Palo Alto; Qianjin Hu, Castro Valley, all of CA (US)

(73) Assignee: Mergen, Ltd., San Leandro, CA (US)

(*) Notice: Subject to any disclaimer, the term of this patent is extended or adjusted under 35 U.S.C. 154(b) by 0 days.

(21) Appl. No.: 09/707,366

(22) Filed: Nov. 6, 2000

Related U.S. Application Data
(60) Provisional application No. 60/191,356, filed on Mar. 22, 2000.

(51) Int. Cl.$^7$ .......................... C12Q 1/68; C12P 19/34; C07H 21/04

(52) U.S. Cl. ..................... 435/6; 435/91.2; 536/24.33

(58) Field of Search .................. 435/6, 91.2, 810; 536/24.33

(56) References Cited

U.S. PATENT DOCUMENTS

| | | |
|---|---|---|
| 5,405,746 A | 4/1995 | Uhlen |
| 5,419,966 A | 5/1995 | Reed et al. |
| 5,436,327 A | 7/1995 | Southern et al. |
| 5,470,967 A | 11/1995 | Huie et al. |
| 5,556,752 A | 9/1996 | Lockhart et al. |
| 5,641,658 A | 6/1997 | Adams et al. |
| 5,643,765 A | 7/1997 | Willey |
| 5,700,637 A | 12/1997 | Southern |
| 5,714,331 A | 2/1998 | Buchardt et al. |
| 5,723,320 A * | 3/1998 | Dehlinger .................. 435/91.1 |
| 5,744,305 A | 4/1998 | Fodor et al. |
| 5,747,251 A | 5/1998 | Carson et al. |
| 5,750,380 A | 5/1998 | Itakura et al. |
| 5,759,779 A * | 6/1998 | Dehlinger ...................... 435/6 |
| 5,770,456 A | 6/1998 | Holmes |
| 5,770,722 A | 6/1998 | Lockhart et al. |
| 5,800,992 A | 9/1998 | Fodor et al. |
| 5,807,522 A | 9/1998 | Brown et al. |
| 5,817,479 A | 10/1998 | Au-Young et al. |
| 5,831,070 A | 11/1998 | Pease et al. |
| 5,837,832 A | 11/1998 | Chee et al. |
| 5,856,174 A | 1/1999 | Lipshutz et al. |
| 5,858,652 A | 1/1999 | Laffler et al. |
| 5,861,242 A | 1/1999 | Chee et al. |
| 5,891,625 A | 4/1999 | Buchardt et al. |
| 5,919,523 A | 7/1999 | Sundberg et al. |
| 5,922,617 A | 7/1999 | Wang et al. |
| 5,928,905 A | 7/1999 | Stemmer et al. |
| 5,948,649 A | 9/1999 | Stewart et al. |
| 5,958,698 A | 9/1999 | Chetverin et al. |
| 6,017,738 A * | 1/2000 | Morris et al. .............. 435/91.2 |
| 6,054,270 A | 4/2000 | Southern |
| 6,150,095 A * | 11/2000 | Southern et al. ................ 435/6 |
| 6,153,379 A * | 11/2000 | Caskey et al. ................. 435/6 |

OTHER PUBLICATIONS

U.S. Application Ser. No. 60/173,618, Hu et al., filed Dec. 29, 1999.

Brown, P. O. and Botstein, D. (Jan. 1999). "Exploring the New World of the Genome with DNA Microarrays," *Nature Genetics Supplement* 21:33–37.

Chakravarti, A. (Jan. 1999). "Population Genetics–Making Sense Out of Sequence," *Nature Genetics Supp.* 21:56–60.

Cho, R. J. et al. (Mar. 1998). "Parallel Analysis of Genetics Selections Using Whole Genome Oligonucleotide Arrays," *Proc. Natl. Acad. Sci. USA* 95:3752–3757.

Collins F. S. et al. (Nov. 28, 1997). "Variations on a Theme: Cataloging Human DNA Sequence Variation," *Science* 278(5343):1580–1581.

Denis, M. et al. (1997). "Development of a Semiquantitative PCR Assay Using Internal Standard and Colorimetric Detection on Microwell Plate for Pseudorabies Virus," *Molecular and Cellular Probes* 11:439–448.

Eliaou, J. et al. (1992). "Generic HLA–DRB1 Gene Oligotyping by a Nonradioactive Reverse Dot–Blot Methodology," *Human Immunology* 35:215–222.

Embretson, J. et al. (Mar. 25, 1993). "Massive Covert Infection of Helper T Lymphocytes and Macrophages by HIV during the Incubation Period of AIDS," *Nature* 362:359–362.

Gosden, J. and Hanratty, D. (1993). "PCR In Situ: A Rapid Alternative to In Situ Hybridization for Mapping Short, Low Copy Number Sequences Without Isotopes," *BioTechniques* 15(1):78–80.

Hacia, J. G. (Jan. 1999). "Resequencing and Mutational Using Oligonucleotide Microarrays," *Nature Genetics Supplement* 21:42–47.

Halford, W. P. (1999). "The Essential Prerequisites for Quantitative RT–PCR," *Nature Biotechnology* 17:835–836.

Heniford, B. W. et al. (1993). "Variation in Cellular EGF Receptor mRNA Expression Demonstrated by in situ Reverse Transcriptase Polymerase Chain Reaction," *Nucleic Acids Research* 21(14):3159–3166.

Kohsaka, H. and Carson, D. A. (1994). "Solid–Phase Polymerase Chain Reaction," *Journal of Clinical Laboratory Analysis* 8:452–455.

Long, A. A. et al. (1993). "Comparison of Indirect and Direct In–situ Polymerase Chain Reaction in Cell Preparations and Tissue Sections," *Histochemistry* 99:151–162.

(List continued on next page.)

Primary Examiner—Kenneth R. Horlick
(74) *Attorney, Agent, or Firm*—Morrison & Foerster LLP (57) ABSTRACT

Solid phase polymerase-mediated amplification approaches using immobilized primers on a microarray are provided for detecting sequence variations in a target polynucleotide. The methods and compositions provided herein are useful for research and clinical applications, particularly for large scale assays of genetic information in biological samples of interest.

30 Claims, 2 Drawing Sheets-

OTHER PUBLICATIONS

Nielsen, P. E. (1999). "Applications of Peptide Nucleic Acids," *Curr. Opin. Biotechnol.* 10:71–75.

Nielsen, P. E. et al. (Dec. 1991). "Sequence–Selective Recognition of DNA by Strand Displacement with a Thymine–Substituted Polyamide," *Science* 254:1497–1500.

Nuovo, G. J. et al. (1993). "Importance of Different Variables for Enhancing In Situ Detection of PCR–Amplified DNA," *PCR Methods and Applications* 2(4):305–312.

Patterson, B. K. (May 14, 1993). et al. "Detection of HIV–1 DNA and Messenger RNA in Individual Cells by PCR–Driven in Situ Hybridization and Flow Cytometry," *Science* 260:976–979.

Schena, M. et al. (Oct. 20, 1995). "Quantitative Monitoring of Gene Expression Patterns with a Complementary DNA Microarray," *Science* 270:467–470.

Schena, M. et al. (Oct. 1996). "Parallel Human Genome Analysis: Microarray–Based Expression Monitoring of 1000 Genes," *Proc. Natl. Acad. Sci. USA* 93:10614–10619.

* cited by examiner

MICROARRAY-BASED ANALYSIS OF POLYNUCLEOTIDE SEQUENCE VARIATIONS

CROSS REFERENCE TO RELATED APPLICATIONS

This Application claims priority of provisional application No. 60/191,356 filed Mar. 22, 2000.

TECHNICAL FIELD OF THE INVENTION

This invention relates generally to the field of nucleic acid biology. More specifically, the invention provides methods and compositions for high-throughput amplification, detection and comparison of polynucleotide sequence variations in biological samples for research, diagnostic and therapeutic applications.

BACKGROUND OF THE INVENTION

As the Human Genome Project approaches completion of a reference sequence of the human genome, increasing attention is being paid to uncovering DNA sequence variations among groups of individuals as well as between different human populations. Identifying these variations is a critical part of further exploration of the genetic basis for predisposition and resistance to disease. These sequence variations will serve as genetic markers in studies of diseases and traits with complex inheritance patterns and strong environmental interactions.

Currently, large-scale sequence assays for population-based genetic variations such as single nucleotide polymorphisms (SNPs) are done on hybridization-based oligonucleotide arrays (DNA chips). For example, U.S. Pat. No. 5,837,832 (Chee et al.) describes DNA chips containing arrays of four sets of probes, each of which differs from others on a single nucleotide. Target polynucleotides of interest are hybridized to the DNA chip and the specific sequence variations detected based on the target polynucleotides' preference and degree of hybridization at discrete probe locations. Similar technology was used in U.S. Pat. No. 5,861,242 (Chee et al.) for analysis of various HIV DNA sequences.

Several problems are associated with the current hybridization-based sequence variation assays, and hence limiting their applications. See review by Hacia (1999) *Nature Genetics Supp.* 21:42–47. For example, accuracy of the hybridization assay remains poor, which hinders its use in heterozygous mutation screens. The same experimental approach applied to any two sequences can yield results with vastly different accuracy. The false negative error rate of the hybridization-based mutational analysis needs to be improved. Since the hybridization-based methodology is hinged on the hybridization differences by one nucleotide, the specificity of hybridization-based sequence analysis can be dramatically influenced by variations in target polynucleotide as well as in hybridization conditions. Hybridization-based mutation detection is particularly powerless when the target polynucleotides are in trace amount in the sample.

Detection of small quantities of genetic materials represents a major challenge in biological research and clinical diagnosis. Polymerase chain reaction (PCR) provides a powerful tool for in vitro amplification of specific polynucleotide sequences, such as genomic DNA, single stranded cDNA or mRNA, with high sensitivity and specificity. One application of this is the amplification of target gene sequences in biological samples from, for example, environmental, food and medical sources, etc. to allow identification of causative, pathogenic, spoilage or indicator organisms present in the sample.

Therefore, there exist a need for developing methods for analyzing sequence variations with higher accuracy and greater sensitivity.

SUMMARY OF THE INVENTION

The present invention provides novel methods for sequence variation analysis with greater sensitivity, better accuracy and less time-consuming, as compared to the conventional hybridization-based approaches.

In one aspect, the invention provides methods for detecting sequence variations between a target polynucleotide and a reference sequence, including single or multiple base substitutions, deletions or insertions, and other more complex variations. The methods utilize an array of multiple groups of oligonucleotide primers immobilized to a solid phase support, with each group of oligonucleotide primers being selected to span a particular region of the reference sequence, occupying a discrete area of the array, and comprising at least four sets of primers: 1) a first set that is exactly complementary to the reference sequence; and 2) three additional sets of primers, each of which is identical to the first set of primers but for the most 3'-end nucleotide which is different in each of the three sets. The array of the invention can be used in a polymerase-mediated amplification reaction, during which the target polynucleotide serves as template for the synthesis of detectable nascent polynucleotides which are extended from the appropriate sets of primers that are exactly complementary to the target polynucleotide. The immobilized primers enable "in-situ" hybridization and amplification of specific regions of the target polynucleotide on a solid-phase support. The nascent strand at each primer site can be detected quantitatively with labels that are incorporated into the strand during amplification. In one preferred embodiment, the amplification means for practicing the invention is PCR. The microarray on a solid phase support can comprise up to about 100,000 groups of primers. As such, the method is useful for detecting up to about 100,000 different regions of the target polynucleotide. For most applications, a high number of groups will be desirable, although it is clear that there is no lower limit to the number of groups which can be present on the support.

According to one embodiment of the invention, an immobilized primer is used alone for asymmetric PCR of a target polynucleotide that will result in a single complementary strand attached to the solid phase at each proper primer site and detected optionally with labels incorporated into the strand. According to another embodiment of the invention, another primer for each target polynucleotide is present in solution so that both strands for a target polynucleotide can be symmetrically synthesized and retained at each primer site for enhanced detection.

The present invention can be used to detect sequence variations in a single target polynucleotide as compared with a reference sequence, in which case the DNA array of the invention comprises multiple groups of primers corresponding and or relating to the reference sequence, as described above. Alternatively, the invention can be used to detect sequence variations in multiple target polynucleotides as compared with one or many reference sequences. The target polynucleotides can be structurally related or unrelated. When multiple target polynucleotides with no sequence homology are detected according to the present invention, the DNA microarray is divided into different areas with each area devoted to a particular reference sequence aimed at a particular target polynucleotide. Multiple groups of primers are affixed onto the solid support within the area, with each group being selected to span a particular region of the reference sequence. As in the case of single target polynucleotide, each group comprises at least four sets of primers: 1) a first set that is exactly complementary to the reference sequence; and 2) three additional sets of primers, each of which is identical to the first set of primers but for the most 3'-end nucleotide which is different in each of the three sets.

The invention further provides kits for detecting sequence variations in a target polynucleotide using either symmetric PCR or asymmetric PCR approach as disclosed herein. The kits comprise a microarray of PCR primers and reagents necessary for PCR reaction and detection. The microarray of primers can comprise up to about 100,000 groups of primers tailored to particular reference sequences. In one embodiment of the invention, the kits comprise labeled nucleotides capable of being incorporated into the synthesized strands during PCR reaction.

MODE(S) FOR CARRYING OUT THE INVENTION

The present invention provides novel methods and compositions for high-throughput fashioned, sensitive yet simple amplification and detection of sequence variations in a target polynucleotide. The invention can be used in various aspects of genome analysis that finds utility in both basic biological research and medical diagnosis and therapeutics.

The present invention is based on a novel combination of PCR and polynucleotide array technology. The basic principle of the invention is that a single nucleotide mismatch between a template and a corresponding primer's 3'-end is sufficient to prevent the elongation of a nascent strand. Therefore, the target polynucleotide will only be amplified at the site where the primer is a perfect match with the target sequence. Some aspects of the primer preparation and PCR amplification procedures are similar to those described in a co-pending U.S. Provisional Application No. 60/173,618 (filed Dec. 29, 1999) and the U.S. Pat. No. 5,837,832 (Chee et al.), disclosures of which are incorporated herein by reference.

A. Definitions

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, etc.), those containing alkylators, those with modified linkages (e.g., alpha anomeric nucleic acids, etc.), as well as unmodified forms of the polynucleotide.

The term "primer", as used herein, refers to an oligonucleotide which is capable of acting as a point of initiation of polynucleotide synthesis along a complementary strand when placed under conditions in which synthesis of a primer extension product which is complementary to a polynucleotide is catalyzed. Such conditions include the presence of four different nucleotide triphosphates or nucleoside analogs and one or more agents for polymerization such as DNA polymerase and/or reverse transcriptase, in an appropriate buffer ("buffer" includes substituents which are cofactors, or which affect pH, ionic strength, etc.), and at a suitable temperature. A primer must be sufficiently long to prime the synthesis of extension products in the presence of an agent for polymerase. A typical primer contains at least about 5 nucleotides in length of a sequence substantially complementary to the target sequence, but somewhat longer primers are preferred. Usually primers contain about 15–26 nucleotides, but longer primers, up to 35 nucleotides, may also be employed.

A primer will always contain a sequence substantially complementary to the target sequence, that is the specific sequence to be amplified, to which it can anneal. A primer may, optionally, also comprise a promoter sequence. The term "promoter sequence" defines a single strand of a nucleic acid sequence that is specifically recognized by an RNA polymerase that binds to a recognized sequence and initiates the process of transcription by which an RNA transcript is produced. In principle, any promoter sequence may be employed for which there is a known and available polymerase that is capable of recognizing the initiation sequence. Known and useful promoters are those that are recognized by certain bacteriophage polymerases, such as bacteriophage T3, T7 or SP6.

As used herein, the term "tag," "sequence tag" or "primer tag sequence" refers to an oligonucleotide with specific nucleic acid sequence that serves to identify a batch of polynucleotides bearing such tags therein. Polynucleotides from the same biological source are covalently tagged with a specific sequence tag so that in subsequent analysis the polynucleotide can be identified according to its source of origin. The sequence tags also serves as primers for nucleic acid amplification reactions.

A "microarray" is a linear or two-dimensional array of preferably discrete regions, each having a defined area, formed on the surface of a solid support. The density of the discrete regions on a microarray is determined by the total numbers of target polynucleotides to be detected on the surface of a single solid phase support, preferably at least about 50/cm$^2$, more preferably at least about 100/cm$^2$, even more preferably at least about 500/cm$^2$, and still more preferably at least about 1,000/cm$^2$. As used herein, a DNA microarray is an array of oligonucleotide primers placed on a chip or other surfaces used to amplify or clone target polynucleotides. Since the position of each particular group of primers in the array is known, the identities of the target polynucleotides can be determined based on their binding to a particular position in the microarray.

A "linker" is a synthetic oligodeoxyribonucleotide which contains a restriction site. A linker may be blunt end-ligated onto the ends of DNA fragments to create restriction sites which can be used in the subsequent cloning of the fragment into a vector molecule.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

The term "amplify" is used in the broad sense to mean creating an amplification product which may include, for example, additional target molecules, or target-like molecules or molecules complementary to the target molecule, which molecules are created by virtue of the presence of the target molecule in the sample. In the situation where the target is a nucleic acid, an amplification product can be made enzymatically with DNA or RNA polymerases or reverse transcriptases.

As used herein, a "biological sample" refers to a sample of tissue or fluid isolated from an individual, including but not limited to, for example, blood, plasma, serum, spinal fluid, lymph fluid, the external sections of the skin, respiratory, intestinal, and genitourinary tracts, tears, saliva, milk, cells (including but not limited to blood cells), tumors, organs, and also samples of in vitro cell culture constituents.

The term "biological sources" as used herein refers to the sources from which the target polynucleotides are derived from. The source can be of any form of "sample" as described above, including but not limited to, cell, tissue or fluid. "Different biological sources" can refer to different cells/tissues/organs of the same individual, or cells/tissues/organs from different individuals of the same species, or cells/tissues/organs from different species.

B. Selecting a Reference Sequence

The present invention can be used to compare a target polynucleotide with a particular reference sequence. The target polynucleotide comprises either the reference sequence itself or variants thereof. The sequence selected as a reference sequence can be from any biological sources, including but not limited to cells, tissues or fluid. The reference sequence and the target polynucleotide can be from different sources. Preferably, the sources for the reference sequence and the target polynucleotide are from different individuals of the same species, or different populations of the same species.

A reference sequence may contain at least a portion of a gene of interest from the particular biological source. Preferably, the reference sequence for the present invention covers a region in which at least one particular nucleotide position is known to be associated with certain functionality of a gene. For example, the position can be an active site of a gene encoding an enzyme, and a point mutation at the position causes the loss of the enzymatic activity. The position can also be a drug resistance site in a bacteria genome, at which a nucleotide substitution of the wild type gene causes the bacteria resistant to certain antibiotics. The reference sequence may also contain the entire genome of the biological source. For example, the entire genome of one HIV strain may be used as the reference sequence for identification of sequence variants of different HIV strains.

The reference sequence can be from an individual representative of a particular human population, and be used to identify SNPs of different populations. Different human populations can be of different sex, age or race, can be from different geographic areas, and can be from different families. Preferably, the reference sequences are selected to represent certain identifiable traits or phenotypes of the population. Further studies on the association of identified sequence variations and these phenotypic traits should provide insights in the genetic linkage of the populations or genetic basis of certain diseases.

The reference sequence can be of any length, usually between about 5, 10, 20, 50, 100, 500, 1000, 5000 or 10,000 bases. The reference sequence may contain some sequence variations itself compared to a wild type gene, so long as the variations is outside of the region of interest for the purpose of the present invention. The reference sequence can be obtained from any sequence sources, such as sequence databases that are either publicly accessible or commercially available.

C. Designing an Array of Oligonucleotide Primers

1. Selecting Primers

The invention provides a prepared solid support comprising immobilized and separate groups of oligonucleotide primers. Each primer group corresponds to a particular region within the reference sequence, and contains at least four sets of primers with the first set being exactly complementary to the particular region of the reference sequence, and the other three sets being identical to the first set but for the most 3'-end nucleotide. For example, for an A nucleotide in the reference sequence, the corresponding primer from the first set has a T at its most 3'-end, while the additional three primer sets have at their most 3'-end an A, C, or G, a different nucleotide in each set. The length of the four primer sets are preferred, although not necessary, to be the same. The primers can be selected or designed using for example a standard PCR primer selection program such as Primer3 from Massachusetts Institute of Technology (MIT).

The solid phase support can provide an areas of about 5 to about 100 square micrometers, on which up to about 100,000 groups of primers can be immobilized in discrete areas according to a predetermined pattern. The prepared solid support can have an associated written or electronic record of the sequence of the primer or primer pairs at any given location on the support, and thus the location on the support of an amplified target can be identified as well.

The number of primers within each group corresponding to a particular region of the reference sequence can be determined and limited by the needs of the subsequent planned amplification reaction on the microarray. Thus, for example, the number of primers deemed necessary for conducting an PCR at a specific site on the microarray, given especially the reaction volume and expected number of target template polynucleotide molecules, and the proposed number of cycles of PCR, will help determine exactly how much oligonucleotide primer copies to apply as a group at each location on the support to ensure successful reactions. Preferably, the amounts of primers (i.e. primer molecule numbers or primer concentration) will be about the same at each provided location on a given solid support (e.g. in a DNA microarray format having from 1000, to 10,000, up to about 100,000 groups of primers to amplify or detect up to about 100,000 regions of the target polynucleotide).

The solid support can be prepared with primer sequences for a particular application based on the polynucleotides to be detected. The oligonucleotide primers can be of any length suitable for a particular PCR, especially considering the sequence and quality of the target polynucleotides to be amplified. As an example, the primers can be from about 4 to about 30 nucleotides in length.

It is understood that a nucleic acid primer of the present invention may contain minor deletions, additions and/or substitutions of nucleic acid bases, to the extent that such alterations do not negatively affect the yield or product obtained to a significant degree.

Oligonucleotide primers can include the naturally-occurring heterocyclic bases normally found in nucleic acids (uracil, cytosine, thymine, adenine and guanine), as well as modified bases and base analogues. Any modified base or base analogue compatible with hybridization of the primer to a target sequence is useful in the practice of the invention.

The sugar or glycoside portion of the primer can comprise deoxyribose, ribose, and/or modified forms of these sugars, such as, for example, 2'-O-alkyl ribose. In a preferred embodiment, the sugar moiety is 2'-deoxyribose; however, any sugar moiety that is compatible with the ability of the primer to hybridize to a target sequence can be used.

In one embodiment, the nucleoside units of the primer are linked by a phosphodiester backbone, as is well known in the art. In additional embodiments, internucleotide linkages can include any linkage known to one of skill in the art that is compatible with specific hybridization of the primer including, but not limited to phosphorothioate, methylphosphonate, sulfamate (e.g., U.S. Pat. No. 5,470,967) and polyamide (i.e., peptide nucleic acids). Peptide nucleic acids are described in Nielsen et al. (1991) Science 254:1497–1500, U.S. Pat. No. 5,714,331, and Nielsen (1999) Curr. Opin. Biotechnol. 10:71–75.

In certain embodiments, the primer can be a chimeric molecule; i e., can comprise more than one type of base or sugar subunit, and/or the linkages can be of more than one type within the same primer.

The primer can comprise a moiety to facilitate hybridization to its target sequence, as are known in the art, for example, intercalators and/or minor groove binders.

Variations of the bases, sugars, and internucleoside backbone, as well as the presence of any pendant group on the primer, will be compatible with the ability of the primer to bind, in a sequence-specific fashion, with its target sequence. A large number of structural modifications, both known and to be developed, are possible within these bounds. Moreover, synthetic methods for preparing the various heterocyclic bases, sugars, nucleosides and nucleotides which form the primer, and preparation of oligonucleotides of specific predetermined sequence, are well-developed and known in the art. A preferred method for oligonucleotide synthesis incorporates the teaching of U.S. Pat. No. 5,419,966.

The oligonucleotide primers can be designed with any special additional moieties or sequences that will aid and facilitate a particular PCR or subsequent manipulations, e.g. isolation of the amplified target polynucleotides. For example, a primer can comprise sequences in addition to those that are complementary to the target sequence. Such sequences are normally upstream (i.e., to the 5'-side) of the target-complementary sequences in the primer. For example, sequences comprising one or more restriction enzyme recognition sites (so-called "linkers" or "adapters"), when present in a primer upstream of target-complementary sequences, facilitate cloning and subsequent manipulation of an amplification product. Other useful sequences for inclusion in a primer include those complementary to a sequencing primer and those specifying a promoter for a bacteriophage RNA polymerase, such as, for example, T3 RNA polymerase, T7 RNA polymerase and/or SP6 RNA polymerase.

In one aspect of the invention, the microarray primers are defined by a tiling method to cover an entire region of interest in the target polynucleotide. For example, a first group of primers are designed so that the sequence of each primer therein corresponds to the most 5'-portion of the region of interest; a second group of primers have sequence that is "shifted" from the first group by one nucleotide towards the 3'-end of the region; and a third group of primers have sequence that is "shifted" from the second group by one nucleotide toward the 3'-end of the region, and etc. In theory, then, the number of groups of primers equals to the number of nucleotides in the region of interest. Of course, within each group of primers that correspond to a particular portion of the region, there are at least four sets of primers with four different 3'-ends as described above. When multiple target polynucleotides are to be detected according to the present invention, each primer group corresponding to a particular target polynucleotide is resided in a discrete area of the microarray.

2. Solid Phase Support

The solid phase support of the present invention can be of any solid materials and structures suitable for supporting nucleotide hybridization and synthesis. Preferably, the solid phase support comprises at least one substantially rigid surface on which the primers can be immobilized and the PCR reaction performed. The solid phase support can be made of, for example, glass, synthetic polymer, plastic, hard non-mesh nylon or ceramic. Other suitable solid support materials are known and readily available to those of skill in the art. The size of the solid support can be any of the standard microarray sizes, useful for DNA microarray technology, and the size may be tailored to fit the particular machine being used to conduct a reaction of the invention. Methods and materials for derivatization of solid phase supports for the purpose of immobilizing oligonucleotides are known to those skill in the art and described in, for example, U.S. Pat. No. 5,919,523, the disclosure of which is incorporated herein by reference.

The solid support can be provided in or be part of a fluid containing vessel. For example, the solid support can be placed in a chamber with sides that create a seal along the edge of the solid support so as to contain the polymerase chain reaction (PCR) on the support. In a specific example the chamber can have walls on each side of a rectangular support to ensure that the PCR mixture remains on the support and also to make the entire surface useful for providing the primers.

3. Primer Immobilization

The oligonucleotide primers of the invention are affixed, immobilized, provided, and/or applied to the surface of the solid support using any available means to fix, immobilize, provide and/or apply the oligonucleotides at a particular location on the solid support. For example, photolithography (Affymetrix, Santa Clara, Calif.) can be used to apply the oligonucleotide primers at particular position on a chip or solid support, as described in the U.S. Pat. Nos. 5,919,523, 5,837,832, 5,831,070, and 5,770,722, which are incorporated herein by reference. The oligonucleotide primers may also be applied to a solid support as described in Brown and Shalon, U.S. Pat. No. 5,807,522 (1998). Additionally, the primers may be applied to a solid support using a robotic system, such as one manufactured by Genetic MicroSystems (Woburn, Mass.), GeneMachines (San Carlos, Calif.) or Cartesian Technologies (Irvine, Calif.).

D. Detecting Sequence Variations in a Target Polynucleotides

In one aspect of the invention, solid phase amplification of target polynucleotides from one biological sample is performed, wherein multiple groups of oligonucleotide primers are immobilized on a solid phase support. In a preferred embodiment, the primers within a group comprises at least a first set of primers that are identical in sequence and are complementary to a defined sequence of the target polynucleotide, capable of hybridizing to the target polynucleotide under appropriate conditions, and suitable as initial primers for nucleic acid synthesis (i.e., chain elongation or extension). Selected primers covering a particular region of the reference sequence are immobilized, as a group, onto a solid support at a discrete location. Preferably, the distance between groups is greater than the resolution of detection means to be used for detecting the amplified products. In a preferred embodiment, the primers are immobilized to form a microarray or chip that can be processed and analyzed via automated, processing. The immobilized primers are used for solid phase amplification of target polynucleotides under conditions suitable for a nucleic acid amplification means.

According to one aspect of the invention, the initial target polynucleotide is in double-stranded form with a sense strand ("positive strand") and a complementary strand ("negative strand"). Prior to conducting amplification, the target polynucleotide undergoes denaturation, such as thermal denaturation, whereby the two strands are denatured and separated in the reaction solution. Preferably, primers used in the invention are in vast molar excess to the estimated concentration of the target polynucleotides to counteract the renaturation of the two target polynucleotide strands. Alternatively, the initial target polynucleotide is a single-strand, be it a single-stranded DNA or RNA.

In one preferred embodiment of the invention, the nucleic acid amplification is mediated by a polymerase. More preferably, the amplification is performed under conditions suitable for a PCR reaction. As understood by those skilled in the art, a PCR reaction generally involves multiple cycles of annealing-elongating-denaturing steps at varied reaction temperatures, during which multiple copies of nascent strands are synthesized based on the initial target polynucleotide as template. As the results, the initial target sequences are "amplified" either linearly or exponentially, depending on the condition and restraints of the PCR reaction.

During the PCR reaction according to the present invention, the array of immobilized primers are contacted with the target polynucleotide in a reaction mixture, following denaturation if the target polynucleotides are in double-stranded form. Under conditions suitable for annealing, the single stranded target polynucleotide is hybridized to an immobilized single primer which contains sequence complementary to a defined sequence region within the single-stranded target polynucleotide. Under conditions suitable for chain elongation (including but not limited to, the presence of DNA polymerase and free nucleotides dNTPs), each target polynucleotide strand serves as an initial template for synthesis of a nascent complementary strand, which is primed from the 3'-hydroxyl of the annealed primer and extended to the 5'-end of the target template. Following the completion of chain elongation, the reaction condition is changed to allow denaturation, during which the target strand and the nascent strand are separated so that the target strand is released into the sample solution and the nascent strand retained on the solid support via the immobilized primer.

In practicing the present invention, the immobilized single primers can be used alone or, alternatively, in combination with primers in the reaction solution that are complementary to the sequence at the 3'-end of the nascent immobilized strands. Furthermore, the solution phase primers can be either universal primers capable of amplifying all the target polynucleotides or, a pool of specific primers, each of which is specific to a particular target sequence.

In one aspect of the invention, there are no solution phase primers used. Accordingly, the initial amplification reaction as described above produces nascent strands affixed to the solid phase support at each primer site, either as a single strand or annealed with an initial target polynucleotide strand, depending upon whether or not a denaturation step is introduced after elongation. And the presence of these nascent strands can be detected by appropriate detection means as further described below.

In another aspect of the invention, solution phase primers are used in combination with the solid phase immobilized primers for the amplification of the multiple target polynucleotides. Subsequent to the initial amplification reaction, another round of amplification reaction is performed, during which the previously formed nascent strand complementary at its 3'-end to the solution phase primers will anneal to the solution phase primers and serve as a template for a subsequent synthesis of a second nascent strand substantially identical to the target polynucleotide. As the result, a double-stranded nascent polynucleotide can be formed and affixed on the solid phase support at each primer site.

For the purpose of the invention, target polynucleotides can be double stranded DNA, single stranded DNA, or RNA. Examples of target polynucleotide include, but are not limited to, genomic DNA, cDNA, mRNA, mitochondria DNA, viral DNA, amplified DNA, and viral RNA. Double-stranded target polynucleotides undergo denaturation at the beginning of the amplification reactions to provide single-stranded templates.

mRNA target polynucleotides can be directly used as templates for amplification mediated by reverse transcriptase. Following the completion of chain elongation originated from each immobilized primer site, the hybridized RNA template strand can be destroyed by, for example, RNAse H, leaving the nascent complementary DNA strand affixed to the solid phase support. If a second primer (either specific or universal) is present in the solution phase, the first nascent cDNA strand will serve as a template for synthesizing another nascent strand, thereby forming a double-stranded nascent DNA molecule at each immobilized primer site or binding two immobilized primers.

Alternatively, mRNA target polynucleotides in a sample can be first reverse-transcribed into complementary DNAs which in turn serve as initial templates for the solid phase PCR reactions of the invention. The reverse transcription can be initiated from, for example, a poly-T universal primer that can also be used as the universal primer in solution phase for a PCR amplification reaction according to the invention. A poly-T initiated cDNA product will anneal at its 3'-end to the specific primer immobilized on the solid phase support and serves as template for subsequent synthesis of a nascent complementary strand having at its 3'-end a poly-A sequences. Following a denaturation step, the single immobilized nascent strand is capable of hybridizing to a poly-T universal primer in the solution phase and serving as template for subsequent round of PCR amplification and formation of double-stranded nascent polynucleotides that are affixed to the solid phase support.

Multiple target polynucleotides of the invention can be from one single biological source or, alternatively, from multiple biological sources such as different species or tissues. For example, a population of target polynucleotides isolated from a healthy individual can be mixed in one PCR reaction with another population of target polynucleotides isolated from a patient with a disease of interest, under conditions that would allow distinguishing amplified products of the two sources by detection methods known in the art, as described in detail above. Therefore, the present invention can be used for a cross-species comparative analysis of target polynucleotides.

5. PCR Reaction

In practicing the invention, a reaction mixture comprising the appropriate target polynucleotides mixed with the reagents necessary for conducting the polymerase chain reaction (PCR) are placed in contact with each immobilized primer pair or single primer population on the solid support. The appropriate target polynucleotides can be double stranded DNA, single stranded cDNA generated by reverse transcription of RNA templates, or mRNA population. The reaction mixture contains an enzyme for facilitating the synthesis of a polynucleotide strand complementary to a target strand, e.g. a polymerase. Suitable polymerases include thermostable polymerase enzymes, such as a Taq DNA polymerase, Tth1 DNA polymerase, Vent DNA polymerase, and Pfu DNA polymerase. The reaction mixture can also contain a label molecule capable of being incorporated into the nascent strands during polymerase chain reaction so that the amplified products can be detected on the solid support after the PCR. The label can be detected directly or indirectly according to methods well known in the art. Suitable labels for direct detection can be any fluorescent molecules such as fluorescein isothiocyanate, Texas red or rhodamine. Molecules facilitating indirect detection, such as biotin or digoxigenin, can also be incorporated into the nascent strands during the PCR. Biotin can be subsequently detected by binding to a labeled streptavidin or a labeled anti-biotin antibody. Likewise, incorporated digoxigenin can be detected by a labeled or unlabeled anti-digoxigenin antibody, and the unlabeled anti-digoxigenin antibody can be detected by binding a labeled anti-anti-digoxigenin antibody.

After the reagents for conducting the PCR contact the immobilized primers on the microarray, the microarray is placed in conditions that facilitate the PCR to take place, using for example an automated system such as an in situ PCR machine. The reaction conditions for the PCR procedure can be as recommended by the in situ PCR machine manual, and may be varied as appropriate given the nature of the templates being used or any other difficulties anticipated with the primers and template hybridization. Temperatures and number of cycles can be selected as recommended and as appropriate given the primer selection and the template sequences, and any other relevant factors. The in situ-type PCR reactions on the microarrays can be conducted essentially as described in e.g. Embretson et al, *Nature* 362:359–362 (1993); Gosden et al, *BioTechniques* 15(1):78–80 (1993); Heniford et al *Nuc. Acid Res.* 21(14) :3159–3166 (1993); Long et al, *Histochemistry* 99:151–162 (1993); Nuovo et al, *PCR Methods and Applications* 2(4) :305–312 (1993); Patterson et al *Science* 260:976–979 (1993).

6. Labeling and Detection

The PCR methods of the invention provide for detection of multiple target polynucleotides in a sample. After the PCR is completed in the presence of appropriate labeling reagents, the amplified and labeled target polynucleotides can be detected at each of the original primer locations on the microarray. Detecting the amplified or labeled target polynucleotides can be conducted by standard methods used to detect the labeled sequences, including, for example, detecting labels that have been incorporated into the amplified or newly synthesized DNA strands. Thus, for example fluorescent labels or radiolabels can be detected directly. Other labeling techniques may require that a label such as biotin or digoxigenin that is incorporated into the DNA during strand synthesis be detected by an antibody or other binding molecule (e.g. streptavidin) that is either labeled or which can bind a labeled molecule itself, for example, a labeled molecule can be e.g. an anti-streptavidin antibody or anti-digoxigenin antibody conjugated to either a fluorescent molecule (e.g. fluorescein isothiocyanate, Texas red and rhodamine), or conjugated to an enzymatically activatable molecule. Whatever the label on the newly synthesized molecules, and whether the label is directly in the DNA or conjugated to a molecule that binds the DNA (or binds a molecule that binds the DNA), the labels (e.g. fluorescent, enzymatic, chemiluminescent, or colorimetric) can be detected by a laser scanner or a CCD camera, or X-ray film, depending on the label, or other appropriate means for detecting a particular label.

The target polynucleotide can be detected by using labeled nucleotides (e.g. dNTP-fluorescent label for direct labeling; dNTP-biotin or dNTP-digoxigenin for indirect labeling) are incorporated into amplified DNA during the PCR. For indirectly labeled DNA, the detection is carried out by fluorescence or other enzyme conjugated streptavidin or anti-digoxigenin antibodies. The PCR method employs detection of the polynucleotides by detecting incorporated label in the newly synthesized complements to the polynucleotide targets. For this purpose, any label that can be incorporated into DNA as it is synthesized can be used, e.g. fluoro-dNTP, biotin-dNTP, or digoxigenin-dNTP, as described above and are known in the art. PCR amplification conducted using one or more universal primers in solution provides the option to detect the amplified targets at locations on the solid support by detecting the universal primers. Thus, where more than one universal primer is used, target strands from different sources can be differentially detected on the solid support.

In a differential expression system, amplification products derived from different biological sources can be detected by differentially labeling the amplified strands based on their origins, as described in the section under "C. Comparing Differential Expression of Genes from Different Biological Sources." In one aspect, the detection methods used herein are different from the detection method for single-source targets, in that the differential labels (e.g., red dye and green dye) are pre-incorporated on the primer tags in solution, rather than being incorporated into the nascent strands during the amplification. Alternatively, a third label can also be incorporated into the nascent strand during amplification, in addition to the differential labels, so that the overall sensitivity for differential expression comparison is enhanced.

7. Detection Kits

The invention provides kits for practicing the methods of the invention. The kit can include, e.g. the materials and reagents for detecting a plurality of target polynucleotides that are otherwise difficult to detect on a solid support. The kit can include e.g. a solid support, oligonucleotide primers for a specific set of target polynucleotides, polymerase chain reaction reagents and components, e.g. enzymes for DNA synthesis, labeling materials, and other buffers and reagents for washing. The kit may also include instructions for use of the kit to amplify specific targets on a solid support. Where the kit contains a prepared solid support having a set of primers already fixed on the solid support, e.g. for amplifying a particular set of target polynucleotides, the design and construction of such a prepared solid support is described above. Such solid supports can be custom-made for individual kits depending on the target polynucleotides the customer desires to detect. The kit also includes reagents necessary for conducting a PCR on a solid support, for example using an in situ-type or solid phase type PCR procedure where the support is capable of PCR amplification using an in situ-type PCR machine. The support can be contacted with the reagents for PCR. A sample potentially containing multiple target polynucleotides is added to the PCR reagent mixture before the reaction. The PCR reagents include the usual PCR buffers, a thermostable polymerase (e.g. Taq DNA polymerase), nucleotides (e.g. dNTPs), and other components and labeling molecules (e.g. for direct or indirect labeling as described above). The solid support provides the affixed primers in designated locations on the solid support. For conducting the PCR, the support with the immobilized primers is contacted with reagents for conducting PCR and the target polynucleotide templates in a reaction mix and the subjected to PCR (e.g. in situ type or solid phase type PCR) conditions. The instructions for use of the kits can include, e.g. such details for the procedure as indicated in the description of the methods above. The kits can be assembled to support practice of the PCR amplification method using immobilized primers alone or, alternatively, together with solution phase primers.

D. High Throughput Assay of Multiple Target Polynucleotides

The amplification methods described above can be used for a high throughput assay of multiple target polynucleotides on a single solid phase support. Multiple groups of primers, either in single form or in pairs, are immobilized onto a solid phase support to form a microarray with predetermined pattern. Each group of primers correspond to a particular target polynucleotide and occupies a discrete position within the microarray. When a sample containing or suspected of containing multiple target polynucleotides is in contact with the microarray under reaction conditions suitable for PCR reactions as described above, each target polynucleotide will be amplified and affixed at a discrete position with the microarray having corresponding primers immobilized thereto.

According to the invention, the number of potential target polynucleotides is limited only by the available technology for producing and analyzing small dense microarrays. For example, using known technologies up to about 100,000 polynucleotides may be analyzed on a single solid support by providing up to about 100,000 different groups of primer pairs at discrete locations on the solid support, and contacting the support with a PCR solution and a sample comprising at least one copy of the target polynucleotides that the primers are designed to detect.

EXAMPLES

Example 1

PCR Detection of the G3PDF Gene on Microarrays

A gene encoding human G3PDH was selected for detection by amplification on a microarray, either by a symmetric PCR in which both members of a primer pair are immobilized onto the support, or by an asymmetric PCR in which one member of the primer pair is immobilized and another member is in solution.

Based on the known sequence of human G3PDH (hG3PDH), four sets of primers were designed and used for the assay. The four sets of primers have identical hG3PDH gene sequence except for the last base at their most 3'-end, where each set has a different nucleotide, A, T, C, or G. The primers were synthesized with a 5'-end modification of amine to aid in affixing the primers to the solid support. The primers were spotted in pairs or as single primers, at different concentrations, on a silanated glass slide purchased from Sigma Chemicals (St. Louis, Mo).

The silanated slides with the provided primers were hydrated overnight in saturated NaCl chamber at room temperature. The hydrated slides were rinsed with 4×SSC for 5 minutes and then washed with water. The slides were blocked with SurModics (Madison, Wis.) blocking solution (with 0.1% SDS) for 15 minutes at 50° C., and then rinsed with water 2× and dried by air. The slides were then ready for use.

The PCR reaction solution was prepared to give a final concentration at 200 $\mu$M each dATP, dGTP, and dTTP; 100 $\mu$M dCTP and 100 $\mu$M Biotin-14-dCTP. The reaction solution also contains 1×Taq reaction buffer (with 1.5 mM MgCl$_2$); human G3PDH gene plasmids as DNA templates (100 ng phagemid DNA or 500 ng ss-cDNA library) and 2.5 units of Taq polymerase enzyme. 70 $\mu$l reaction solutions was generated as follows:

| | |
|---|---|
| 7 $\mu$l | 2 mM d3TP (dATP, dGTP, and dTTP) |
| 12.5 $\mu$l | 0.4 mm dCTP |
| 12.5 $\mu$l | 0.4 mM biotin-14-dCTP |
| 7 $\mu$l | 10X reaction buffer (with 15 mM MgCl$_2$) |
| 5 $\mu$l | DNA template |
| 25.5 $\mu$l | water |
| 0.5 $\mu$l | 5 units/$\mu$l of Taq DNA Polymerase for a total volume of 70 $\mu$l. |

A HyBaid chamber (HyBaid USA, Franklin, Mass.) was placed on the slide to keep the arrayed locations in the center, and the reaction solution was transferred to the chamber and sealed with a plastic cover. The PCR machine was pre-warmed, and the following cycling protocol was applied:

| | | |
|---|---|---|
| beginning | 94° C. | 5 minutes |
| main cycle: (steps 1–3) repeat 35 × | | |
| step 1 | 94° C. | 30 seconds |
| step 2 | 55° C. | 30 seconds |
| step 3 | 72° C. | 30 seconds |
| final extension | 72° C. | 7 minutes |
| end | 4° C. | hold |

After the PCR was completed, the slide was blocked with a digoxigenin-blocking solution from Boehringer Mannheim (Indianapolis, Ind.) for 30 minutes at room temperature. The slide was stained with Streptavidin (5 $\mu$g/$\mu$l) (1:250 dilution with digoxigenin-blocking solution) for 30 minutes at room temperature with gentle shaking. Digoxigenin-washing buffer was used to wash the slide for 15 minutes at room temperature, twice. The slide was blocked with digoxigenin-blocking solution for 30 minutes at room temperature.

The slide was incubated with the first antibody (rabbit anti-streptavidin) diluted 1:100 in digoxigenin-blocking solution for 1 hour at room temperature. The slide was washed with digoxigenin-washing buffer for 15 minutes at room temperature, twice. The slide was incubated with the second antibody (Cy3 conjugated goat anti-rabbit antibody) diluted 1:100 in digoxigenin-blocking solution for 30 minutes at room temperature. The slide was washed with digoxigenin-washing buffer for 15 minutes at room temperature, twice. The slide was scanned with green beam from Genetic MicroSystems, GMS418.

Figure 1:
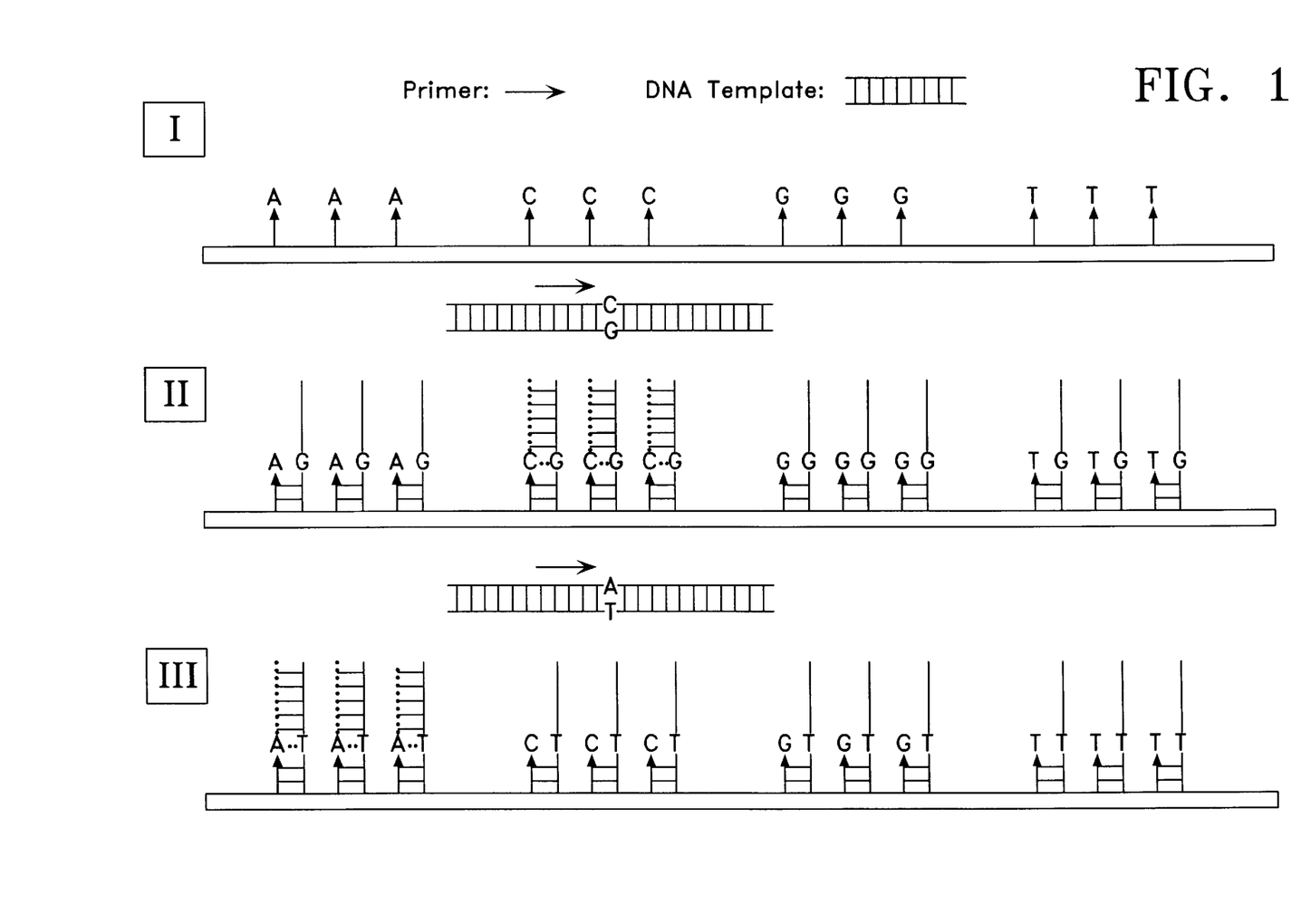
FIG. 1 depicts schematically a solid phase amplification methods for amplifying and detecting sequence variations in a target polynucleotide, using immobilized primers.
Figure 2:
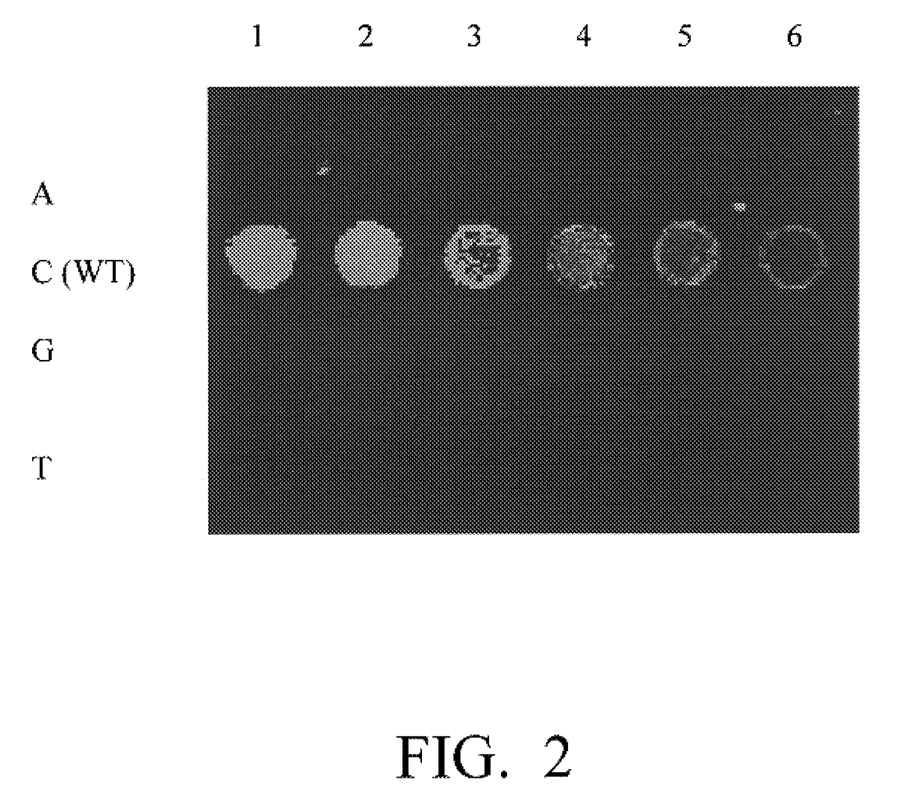
FIG. 2 shows the results of solid phase amplification of human G3PDF gene templates using four sets of primers having one nucleotide difference at the 3'-end.

The results of the symmetric PCR is shown in FIG. 2. 50 ng of G3PDH DNA fragments were used as PCR templates and the primer concentrations from column 1 through 6 were 250, 125, 62, 31, 15 and 7.8 pmol/µl respectively. PCR was carried out under standard protocol for 15 cycles in the presence of biotinylated dCTP and the signal was detected using Strepavidin and Cy3 conjugated antibodies. The illuminated spots indicate successful amplification of the hG3PDH template at the spots where the wild type hG3PDH primers having a C residue at the 3'-end are immobilized. In contrast, no detection of the target hG3PDH template is detectable at any spots where hG3PDH primers with different 3'-end nucleotides were immobilized.

All publications and patent applications cited in this specification are hereby incorporated by reference as if each individual publication or patent application were specifically and individually indicated to be incorporated by reference in their entirety.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying sequence variations in a target polynucleotide in a sample as compared to a reference sequence, the method comprising the steps of:
    a) contacting an array of one or more groups of oligonucleotide primers with a reaction mixture containing the sample and reagents for polymerase-mediated polynucleotide amplification, wherein the array of oligonucleotide primers is immobilized on a solid phase support by the 5'-ends of the oligonucleotides, and further wherein each group of oligonucleotide primers is selected to span a particular region of the reference sequence, occupy a discrete area on the array, and comprise at least two sets of primers: 1) a first set that is exactly complementary to the reference sequence; and 2) one or more additional sets, each of which is identical to the first set of primers but for the nucleotide at the 3'-end which is different in each additional set;
    b) performing a plurality of cycles of polymerase-mediated polynucleotide amplification, whereby the target polynucleotide serves as template for the synthesis of detectable nascent polynucleotides which are extended from the sets of primers that are exactly complementary to the target polynucleotide, wherein all of the oligonucleotide primers of the array are present in the same amplification reaction;
    c) detecting the presence of synthesized polynucleotides which are captured on discrete areas of the solid phase support via corresponding immobilized primers; and
    d) identifying sequence variations in the at least one target polynucleotide according to a detected pattern of synthesized polynucleotides on the solid phase support.

2. The method of claim 1, wherein the reaction mixture further comprises a population of solution phase primers.

3. The method of claim 2, wherein the population of solution phase primers includes an universal primer.

4. The method of claim 3, wherein the universal primer is an oligo-dT primer.

5. The method of claim 3, wherein the universal primer is a primer containing a T7 promoter, a T3 promoter or an SP6 promoter.

6. The method of claim 2, wherein the population of solution phase primers includes multiple primers each having specific sequences.

7. The method of claim 1, wherein sequence variations in least two different target polynucleotides in a sample are identified.

8. The method of claim 1, wherein the reaction mixture comprises a detectable label that is incorporated into the nascent polynucleotides, thereby making the nascent polynucleotides detectable.

9. The method of claim 8, wherein the detectable label is a fluorescent molecule.

10. The method of claim 8, wherein the detectable label is at least one of radiolabeled-dNTP, fluoro-dNTP, biotinylated dNTP or a digoxigenin-dNTP.

11. The method of claim 8, wherein the detectable label is conjugated to a molecule that binds the nascent polynucleotide.

12. The method of claim 11 wherein the detectable label is conjugated to a molecule that binds a second label incorporated into the nascent polynucleotide.

13. The method of claim 1 which is a method for identifying sequence variations in at least one target polynucleotide in a sample as compared to at least one reference sequence, wherein the array comprises from at least about 100 to at least about 100,000 groups of immobilized oligonucleotide primers, and wherein each group of oligonucleotide primers is selected to span a particular region of one of the at least one reference sequences.

14. The method of claim 13, wherein the array comprises at least about 1,000 groups of immobilized oligonucleotide primers.

15. The method of claim 14, wherein the array comprises at least about 10,000 groups of immobilized oligonucleotide primers.

16. The method of claim 1, wherein the solid phase support is made of material selected from the group consisting of glass, plastics, synthetic polymers, ceramic and nylons.

17. The method of claim 1, wherein the polymerase is Taq polymerase, TthI polymerase, Vent polymerase, Pfu polymerase or any other thermostable polymerase.

18. A kit for identifying sequence variations in a target polynucleotide as compared to a reference sequence, comprising:
    a) an array of multiple groups of oligonucleotide primers immobilized to a solid phase support, wherein each group of oligonucleotide primers is selected to span a particular region of the reference sequence, occupying a discrete area of the array, and comprising at least four sets of primers: 1) a first set that is exactly complementary to the reference sequence; and 2) three additional sets of primers, each of which is identical to the first set of primers but for the nucleotide at the 3'-end, which is different in each of the three sets;
    b) reagents suitable for a polymerase-mediated polynucleotide amplification reaction on the array; and
    c) detection means for detecting amplified polynucleotides on the array.

19. The kit of claim 18, wherein the detection means comprises a detectable label that is incorporated into the amplified polynucleotides during the amplification reaction.

20. The kit of claim 19, wherein the detectable label is a fluorescent molecule.

21. The kit of claim 19, wherein the detectable label is a biotinylated 11-dNTP or a digoxigenin-dNTP.

22. An array for identifying sequence variations in at least one target polynucleotide in a sample as compared to at least one reference sequence by polymerase-mediated polynucleotide amplification, the array comprising:

about 100 to about 100,000 groups of oligonucleotide primers immobilized on discrete areas of a solid phase support, wherein the group of oligonucleotide primers is selected to span a particular region of one of the at least one reference sequences, each group comprising:

at least two sets of primers wherein 1) a first set is exactly complementary to the reference sequence, and 2) each of one or more additional sets is identical to the first set of primers except for the nucleotide at the 3'-end which is different in each additional set, such that the target polynucleotide serves as template for the synthesis of detectable nascent polynucleotides extended from the sets of primers that are exactly complementary to the target polynucleotide.

23. The array of claim 22, wherein the array comprises at least about 1,000 groups of immobilized oligonucleotide primers.

24. The array of claim 23, wherein the array comprises at least about 10,000 groups of immobilized oligonucleotide primers.

25. The array of claim 22, wherein the solid phase support is made of material selected from the group consisting of glass, plastics, synthetic polymers, ceramic and nylons.

26. The array of claim 22, wherein the array of oligonucleotide primers is suitable for identifying sequence variations in two or more target polynucleotides.

27. The method of claim 1, wherein each group of oligonucleotide primers of the array comprises four sets of primers: 1) a first set that is exactly complementary to the reference sequence; and 2) three additional sets, each of which is identical to the first set of primers but for the nucleotide at the 3'-end which is different in each additional set.

28. A kit for identifying sequence variations in at least one target polynucleotide as compared to at least one reference sequence, comprising:

a) an array of from about 100 to about 100,000 groups of oligonucleotide primers immobilized to a solid phase support, wherein each group of oligonucleotide primers is selected to span a particular region of one of the at least one reference sequence, occupying a discrete area of the array, and comprising at least two sets of primers: 1) a first set that is exactly complementary to the reference sequence; and 2) one or more additional sets of primers, each of which is identical to the first set of primers but for the nucleotide at the 3'-end, which is different in each additional set;

b) reagents suitable for a polymerase-mediated polynucleotide amplification reaction on the array; and c) detection means for detecting amplified polynucleotides on the array.

29. A kit for identifying sequence variations in a target polynucleotide as compared to a reference sequence, comprising:

a) an array of multiple groups of oligonucleotide primers immobilized to a solid phase support, wherein each group of oligonucleotide primers is selected to span a particular region of the reference sequence, occupying a discrete area of the array, and comprising at least two sets of primers: 1) a first set that is exactly complementary to the reference sequence; and 2) one or more additional sets of primers, each of which is identical to the first set of primers but for the nucleotide at the 3'-end, which is different in each additional set;

b) reagents suitable for polymerase-mediated polynucleotide amplification on the array of both strands of the target polynucleotide, wherein the reagents comprise at least one solution-phase oligonucleotide primer; and c) detection means for detecting amplified polynucleotides on the array.

30. An array for identifying sequence variations in a target polynucleotide in a sample as compared to a reference sequence by polymerase-mediated polynucleotide amplification, the array comprising:

one or more groups of oligonucleotide primers immobilized on discrete areas of a solid phase support, wherein the group of oligonucleotide primers is selected to span a particular region of the reference sequence, each group comprising:

four sets of primers wherein 1) a first set is exactly complementary to the reference sequence, and 2) each of three additional sets is identical to the first set of primers except for the nucleotide at the 3'-end which is different in each additional set, such that the target polynucleotide serves as template for the synthesis of detectable nascent polynucleotides extended from the sets of primers that are exactly complementary to the target polynucleotide.

* * * * *